United States Patent
Dijk

(10) Patent No.: US 8,571,675 B2
(45) Date of Patent: Oct. 29, 2013

(54) DETERMINING OPERATING PARAMETERS FOR A STIMULATING MEDICAL DEVICE

(75) Inventor: Bastiaan van Dijk, Mechelen (BE)

(73) Assignee: Cochlear Limited, Macquarie University, NSW (AU)

( * ) Notice: Subject to any disclaimer, the term of this patent is extended or adjusted under 35 U.S.C. 154(b) by 685 days.

(21) Appl. No.: 11/785,887

(22) Filed: Apr. 20, 2007

(65) Prior Publication Data

US 2007/0255344 A1    Nov. 1, 2007

Related U.S. Application Data

(60) Provisional application No. 60/793,617, filed on Apr. 21, 2006.

(51) Int. Cl.
*A61N 1/36* (2006.01)

(52) U.S. Cl.
USPC .................................................. 607/57

(58) Field of Classification Search
USPC .................. 607/55–57; 600/379, 559
See application file for complete search history.

(56) References Cited

U.S. PATENT DOCUMENTS

| | | |
|---|---|---|
| 4,114,627 A | 9/1978 | Lewyn et al. |
| 4,305,396 A | 12/1981 | Wittkampf et al. |
| 4,343,312 A | 8/1982 | Cals et al. |
| 4,373,531 A | 2/1983 | Wittkampf et al. |
| 4,532,930 A | 8/1985 | Crosby et al. |
| 4,543,956 A | 10/1985 | Herscovici |
| 4,895,152 A | 1/1990 | Callaghan et al. |
| 4,941,179 A | 7/1990 | Bergenstoff et al. |
| 5,016,280 A | 5/1991 | Engebretsch |
| 5,034,918 A | 7/1991 | Joeng |
| 5,172,690 A | 12/1992 | Nappholz et al. |
| 5,271,397 A | 12/1993 | Seligman et al. |
| 5,277,694 A | 1/1994 | Leysieffer et al. |
| 5,278,994 A | 1/1994 | Black et al. |

(Continued)

FOREIGN PATENT DOCUMENTS

| | | |
|---|---|---|
| EP | 0 282 336 A2 | 11/1988 |
| EP | 0836363 | 4/1998 |

(Continued)

OTHER PUBLICATIONS

Brown, et al., The Relationship Between EAP and EABR Thresholds and Levels Used to Program the Nucleus 24 Speech Processor: Data from Adults, *Ear and Hearing*, vol. 21 (2), Apr. 2000, pp. 151-163.

(Continued)

*Primary Examiner* — Carl H Layno
*Assistant Examiner* — Erica Lee
(74) *Attorney, Agent, or Firm* — Kilpatrick, Townsend & Stockton, LLP

(57) ABSTRACT

The measurement of recipient-specific operating parameters for each of a plurality of stimulation channels of a stimulating medical device. Generally, a recipient-specific operating parameter is measured for selected stimulation channels. These measured values are then used to estimate the same operating parameter for the remaining stimulation channels. For each such remaining stimulation channel, the accuracy of the estimated operating parameter value is determined, resulting in the estimated operating parameter value being deemed either valid or invalid. The validated values are retained while in invalidated values are replaced with a directly-measured or re-estimated operating parameter value.

10 Claims, 9 Drawing Sheets

(56) References Cited

U.S. PATENT DOCUMENTS

| | | | |
|---|---|---|---|
| 5,626,629 A * | 5/1997 | Faltys et al. | 607/57 |
| 5,674,264 A | 10/1997 | Carter et al. | |
| 5,748,651 A | 5/1998 | Sheynblat | |
| 5,758,651 A | 6/1998 | Nygard et al. | |
| 5,895,416 A | 4/1999 | Barreras et al. | |
| 5,963,904 A | 10/1999 | Lee et al. | |
| 6,002,966 A | 12/1999 | Loeb et al. | |
| 6,157,861 A * | 12/2000 | Faltys et al. | 607/57 |
| 6,205,360 B1 | 3/2001 | Carter et al. | |
| 6,289,247 B1 | 9/2001 | Faltys et al. | |
| 6,428,484 B1 | 8/2002 | Battmer et al. | |
| 6,430,402 B1 | 8/2002 | Agahi-Keshen | |
| 6,463,328 B1 | 10/2002 | John | |
| 6,537,200 B2 | 3/2003 | Leysieffer et al. | |
| 6,565,503 B2 | 5/2003 | Leysieffer et al. | |
| 6,575,894 B2 | 6/2003 | Leysieffer et al. | |
| 6,600,955 B1 | 7/2003 | Zierhofer | |
| 6,697,674 B2 | 2/2004 | Leysieffer | |
| 6,731,767 B1 | 5/2004 | Blamey et al. | |
| 6,751,505 B1 | 6/2004 | Van Den Honert et al. | |
| 7,043,303 B1 | 5/2006 | Overstreet | |
| 2001/0049466 A1 | 12/2001 | Baumann et al. | |
| 2002/0026091 A1 | 2/2002 | Leysieffer | |
| 2004/0098063 A1 | 5/2004 | Goetz | |
| 2005/0015133 A1 | 1/2005 | Ibrahim et al. | |
| 2005/0101878 A1 * | 5/2005 | Daly et al. | 600/559 |
| 2005/0107845 A1 * | 5/2005 | Wakefield et al. | 607/57 |
| 2005/0245991 A1 | 11/2005 | Faltys et al. | |
| 2006/0235332 A1 | 10/2006 | Smoorenburg | |
| 2007/0084995 A1 * | 4/2007 | Newton et al. | 250/282 |
| 2008/0319508 A1 | 12/2008 | Botros et al. | |
| 2009/0043359 A1 | 2/2009 | Smoorenburg | |

FOREIGN PATENT DOCUMENTS

| | | |
|---|---|---|
| WO | WO 92/10134 | 6/1992 |
| WO | WO 93/24176 | 12/1993 |
| WO | WO 94/14376 | 7/1994 |
| WO | WO 95/01709 | 1/1995 |
| WO | WO 96/12383 | 4/1996 |
| WO | WO 97/09863 | 3/1997 |
| WO | WO 97/48447 | 12/1997 |
| WO | 0052963 | 9/2000 |
| WO | WO 00/76436 | 12/2000 |
| WO | WO 01/13991 | 3/2001 |
| WO | 0156521 | 8/2001 |
| WO | WO 02/082982 | 10/2002 |
| WO | 03070322 | 8/2003 |
| WO | WO 03/070322 | 8/2003 |
| WO | 2004004412 | 1/2004 |
| WO | WO 2004/021885 | 3/2004 |
| WO | 2004080532 | 9/2004 |
| WO | 2005006808 | 1/2005 |
| WO | 2005122887 | 12/2005 |
| WO | 2009124035 | 10/2009 |

OTHER PUBLICATIONS

Charasse, et al., "Automatic analysis of auditory nerve electrically evoked compound action potential with an artificial neural network," *Artificial Intelligence in Medicine*, 2004 31, 221-229.

Delgado, et al, "Automated Auditory Brainstem Response Interpretation," *IEEE Engineering in Medicine and Biology*, Apr./May 1994.

Charasse, et al., "Comparison of Two Different Methods to Automatically Classify Auditory Nerve Responses Recorded with NRT System," *Acta Acustica United with Acustica*, vol. 99 (2004) 512-519.

Seyle, et al., "Speech Perception Using Maps Based on Neural Response Telemetry Measures," *Ear & Hearing*, Copyright © 2002 by Lippincott Williams & Wilkins.

Vannier, et al., "Objective detection of brainstem auditory evoked potentials with a priori information from higher presentation levels," *Artificial Intelligence in Medicine* 25, (2002) 283-301.

Franck, et al., Estimation of Psychophysical Levels Using the Electrically Evoked Compound Action Potential Measured with the Neural Response Telemetry Capabilities of Cochlear Corporation's C124M Device, *Ear & Hearing*, Copyright © 2001 by Lippincott Williams & Wilkins.

Dijk, et al., "Development of a prototype fully-automated intraoperative ECAP recording tool, using NRT™ v3," Cochlear Technology Centre Europe, Mechelen, Belgium, and Laboratoire Neurosciences et Systémes Sensoriels, Lyon France.

Hughes, et al, Comparison of EAP Thresholds with MAP Levels in the Nucleus 24 Cochlear Implant: Data from Children [Articles], *Ear and Hearing*, vol. 21 (2), Apr. 2000, pp. 164-174.

Abbas, et al., "Electrically Evoked Compound Action Potentials Recorded from Subjects Who Use the Nucleus C124M Device," *Gantz et al. Seventh Symposium on Cochlear Implants in Children*.

Baumgarte, et al., "A Nonlinear Psychoacoustic Model Applied to the ISO MPEG Layer 3 Coder," *Institut für Theoretische Nachrichtentechnik und Informationsverarbeitung*, Universität Hannover, Germany.

Edler, et al., "ASAC-Analysis/Synthesis Audio Codec for Very Low Bit Rates," *Institut für Theoretische Nachrichtentechnik und Informationsverarbeitung*, Universität Hannover, Germany.

Cohen, et al., "Spatial spread of neural excitation in cochlear implant recipients: comparison of improved ECAP method and psychophysical forward masking," *Hearing Research*, 179 (2003) 72-87.

Cohen, et al., "Spatial spread of neural excitation: comparison of compound action potential and forward-masking data in cochlear implant recipients," *International Journal of Audiology 2004*: 43: 346-355.

Miller, et al., "An Improved Method of Reducing Stimulus Artifact in the Electrically Evoked Whole-Nerve Potential," *Ear & Hearing*, Copyright © 2000 by Lippincott Williams & Wilkins, USA.

European Search Report, EP 01 95 9971, dated Aug. 11, 2005.

International Preliminary Examination Report, PCT/AU01/01032, dated Apr. 10, 2002.

International Search Report, PCT/AU01/01032, dated Oct. 5, 2001.

International Search Report and Written Opinion, PCT/US05/21207 dated Feb. 8, 2006.

International Preliminary Examination Report, PCT/AU02/00500, dated Feb. 12, 2003.

International Search Report, PCT/AU02/00500, dated Jun. 26, 2002.

Supplementary Partial European Search Report, EP 02 71 7863 dated Oct. 18, 2005.

European Patent Office, "Supplemental European Search Report," issued in connection with European Patent Application No. 05762889.3, on May 11, 2010 (3 pages).

Diller et al., "Measurement of the Electrically Evoked Compound Action Potential Via a Neural Response Telemetry System," vol. 111, No. 5, Annals of Otology, Rhinology & Laryngology, May 2002 (8 pages).

Franck, Kevin H., "A Model of a Nucleus 24 Cochlear Implant Fitting Protocol Based on the Electrically Evoked Whole Nerve Action Potential," Ear and Hearing, 2002 (5 pages).

Lai et al., "A Simple Two-Component Model of the Electrically Evoked Compound Action Potential in the Human Cochlea," Aurology and Neuro-Otology, Nov. 2000 (13 pages).

Nicolai et al., "Performance of Automatic Recognition Algorithms in Nucleus Neural Response Telemetry (NRT)," (1 page).

Smoorenburg et al., Speech Perception in Nucleus C124M Cochlear Implant Users with Processor Settings Based on Electrically Evoked Compound Action Potential Thresholds, Aurology and Neuro-Otology, Nov. 2002 (13 pages).

Thai-Van et al., "Modeling the Relationship Between Psychophysical Perception and Electrically Evoked Compound Action Potential Threshold in Young Cochlear Implant Recipients: Clinical Implications for Implant Fitting," International Federation of Clinical Neurophysiology, Jun. 17, 2004 (14 pages).

Riedmiller et al., "A Direct Adaptive Method for Faster Backpropagation Learning: The RPROP Algorithm," IEEE International Conference on Neural Networks, 1993 (6 pages).

(56) References Cited

OTHER PUBLICATIONS

International Preliminary Examining Authority, "International Preliminary Report on Patentability," issued in connection with International Patent Application No. PCT/US2009/038932, mailed on Jun. 21, 2010 (10 pages).
Australian Intellectual Property Office, "Examiner's First Report," issued in connection with Australian Patent Application No. 2005254100, on Dec. 17, 2009 (2 pages).
Hartmann, et al., "Evoked Potentials from the Auditory Nerve Following Sinusoidal Electrical Stimulation of the Cochlea: New Possibilities for Preoperative Testing in Cochlear-Implant Candidates?" Acta Otoloaryngol (Stockh) 1994; 114, Scandinavian University Press ISSN 0001-648, pp. 495-500.
English language translation of "First Office Action," issued by the Austrian Patent Office, in connection with Austrian Patent Application No. 3B A 9165/2003-1, on Mar. 14, 2007 (2 pages).
International Searching Authority, "International Search Report," issued in connection with International Patent Application No. PCT/AU2003/000804, mailed on Aug. 26, 2003 (2 pages).
International Preliminary Examining Authority, "Written Opinion," issued in connection with International Patent Application No. PCT/AU2003/000804, mailed on Oct. 16, 2003 (3 pages).
International Preliminary Examining Authority, "International Preliminary Examination Report," issued in connection with International Patent Application No. PCT/AU2003/000804, on Oct. 12, 2004 (3 pages).
International Searching Authority, "International Search Report," issued in connection with International Patent Application No. PCT/FR2003/000577, mailed on Jul. 4, 2003 (4 pages).
International Preliminary Examining Authority, "International Preliminary Examination Report," issued in connection with International Patent Application No. PCT/FR2003/000577, on May 7, 2004 (12 pages).
International Searching Authority, "International Search Report," issued in connection with International Patent Application No. PCT/US2005/021207, mailed on Feb. 8, 2006 (1 page).
The International Bureau of WIPO, "International Preliminary Report on Patentability," issued in connection with International Patent Application No. PCT/US2005/021207, on Dec. 20, 2006 (4 pages).
International Searching Authority, "International Search Report," issued in connection with International Patent Application No. PCT/US2009/038932, mailed on Jun. 5, 2009 (3 pages).
International Searching Authority, "Written Opinion," issued in connection with International Patent Application No. PCT/US2009/038932, mailed on Jun. 5, 2009 (6 pages).
Abbas et al., "Summary of Results Using the Nucleus CI24M Implant to Record the Electrically Evoked Compound Action Potential," pp. 45-59, vol. 20(1), Feb. 1999 (25 pages).
Brown et al., "Electrically Evoked Whole-Nerve Action Potentials: Data from Human Cochlear Implant Users," Acoustical Society of America, Jun. 19, 1989 (7 pages).

* cited by examiner

DETERMINING OPERATING PARAMETERS FOR A STIMULATING MEDICAL DEVICE

CROSS-REFERENCE TO RELATED APPLICATIONS

The present invention claims priority from U.S. Provisional Patent Application 60/793,617, filed on Apr. 21, 2006, which is hereby incorporated by reference herein.

BACKGROUND

1. Field of the Invention

The present invention relates generally to stimulating medical devices, and more particularly, to determining operating parameters for a stimulating medical device.

2. Related Art

Hearing loss, which may be due to many different causes, is generally of two types, conductive and sensorineural. In some cases, a person may have hearing loss of both types. Conductive hearing loss occurs when the normal mechanical pathways that provide sound to hair cells in the cochlea are impeded, for example, by damage to the ossicles. Conductive hearing loss is often addressed with conventional hearing aids which amplify sound so that acoustic information can reach the cochlea.

Profound deafness, however, is caused by sensorineural hearing loss. This type of hearing loss is due to the absence or destruction of the hair cells in the cochlea which transduce acoustic signals into nerve impulses. Those suffering from sensorineural hearing loss are thus unable to derive suitable benefit from conventional hearing aids. As a result, prosthetic hearing implants such as cochlear™ prostheses (commonly referred to as cochlear™ prosthetic devices, cochlear™ implants, cochlear™ devices, and the like; simply cochlear implants herein) have been developed to provide persons with sensorineural hearing loss with the ability to perceive sound.

Cochlear implants traditionally comprise external and internal components that cooperate with each other to provide sound sensations to a recipient. The external component traditionally includes a microphone that detects environmental sounds, a sound processor that selects and converts certain detected sounds, particularly speech, into a coded signal, a power source such as a battery, and an external transmitter antenna.

The coded signal generated by the sound processor is transmitted transcutaneously to an implanted receiver/stimulator unit, commonly located within a recess of the temporal bone of the recipient. This transcutaneous transmission occurs via the external transmitter antenna which is positioned to communicate with an implanted receiver antenna disposed within the receiver/stimulator unit. This communication transmits the coded sound signal while also providing power to the implanted receiver/stimulator unit. Conventionally, this link has been in the form of a radio frequency (RF) link, although other communication and power links have been proposed and implemented with varying degrees of success.

The implanted receiver/stimulator unit also includes a stimulator that processes the coded signals to generate an electrical stimulation signal to an intra-cochlea electrode assembly. The electrode assembly typically has a plurality of electrodes that apply electrical stimulation to the auditory nerve to produce a hearing sensation corresponding to the original detected sound. Because the cochlea is tonotopically mapped, that is, partitioned into regions each responsive to stimulation signals in a particular frequency range, each electrode of the implantable electrode array is positioned and configured to deliver a stimulation current to a particular region of the cochlea. In the conversion of sound to electrical stimulation, frequencies are allocated to stimulation channels that provide stimulation current to electrodes that lie in positions in the cochlea at or immediately adjacent to the region of the cochlea that would naturally be stimulated in normal hearing. This enables cochlear implants to bypass the hair cells in the cochlea to deliver electrical stimulation directly to auditory nerve fibers, thereby causing the brain to perceive hearing sensations resembling natural hearing sensations.

The effectiveness of a cochlear implant is dependent not only on the device itself but also on the manner in which the device is customized to conform to the hearing characteristics of a specific recipient. This customization process, commonly referred to as "fitting," "programming," or "mapping," involves the collection and determination of certain operating parameters of the device. These operating parameters include, for example, recipient-specific parameters such as the minimum stimulation current level required to evoke a neural response at a given stimulation channel, known as the threshold level (commonly referred to as the "THR" or "T-Level;" "threshold level" herein), or recipient-specific parameters such as the level at which a sound is loud but comfortable, known as the maximum comfort level (commonly referred to as the Most Comfortable Loudness Level, "MCL," "M-Level," or "C-Level;" simply "comfort level" herein) for each stimulation channel. The threshold and comfort levels, and perhaps other operating parameters, are utilized by a cochlear implant to adjust the stimulation current to attain a desired level of stimulation for a particular recipient.

SUMMARY

In accordance with one aspect of the present invention, an apparatus is disclosed, the apparatus constructed and arranged to determine operating parameter values for each of a plurality of stimulation channels of a cochlear implant, the apparatus configured to measure values of the operating parameter for selected stimulation channels of the cochlear implant, and further configured to interpolate the measured values to derive an estimated value of the operating parameter for one or more non-selected stimulation channels of the cochlear implant.

In accordance with another aspect of the present invention, a method for determining an operating parameter for each of a plurality of stimulation channels of a stimulating medical device is disclosed, the method comprising: measuring the value of the operating parameter for first and second stimulation channels; and stimulating the value of the operating parameter for a third stimulation channel using the measured operating parameter values for the first and second stimulation channels.

In accordance with a further aspect of the invention, an apparatus constructed and arranged to determine operating parameter values for each of a plurality of stimulation channels of a cochlear implant, the apparatus comprising: means for measuring the value of the operating parameter for first and second stimulation channels; and means for estimating the value of the operating parameter for a third stimulation channel using the measured operating parameter values for the first and second stimulation channels.

BRIEF DESCRIPTION OF THE DRAWINGS

Embodiments of the present invention are described below in conjunction with the accompanying drawings, in which.

DETAILED DESCRIPTION

Aspects of the present invention are generally directed to the measurement of recipient-specific operating parameters for each of a plurality of stimulation channels of a stimulating medical device. Generally, a recipient-specific operating parameter is measured for selected stimulation channels. These measured values are then used to estimate the same operating parameter for the remaining stimulation channels. For each such remaining stimulation channel, the accuracy of the estimated operating parameter value is determined, resulting in the estimated operating parameter value being deemed either valid or invalid. The validated values are retained while in invalidated values are replaced with a directly-measured or re-estimated operating parameter value.

Specific embodiments of the present invention are implemented in a stimulating prosthetic hearing implant such as a cochlear™ implant (also commonly referred to as cochlear™ prostheses, cochlear™ devices, cochlear™ implant devices, and the like; generally and collectively referred to as "cochlear implants" herein). An illustration of an exemplary cochlear implant with which embodiments of the present invention may be advantageously operate is depicted in FIG. 1.

Figure 1:
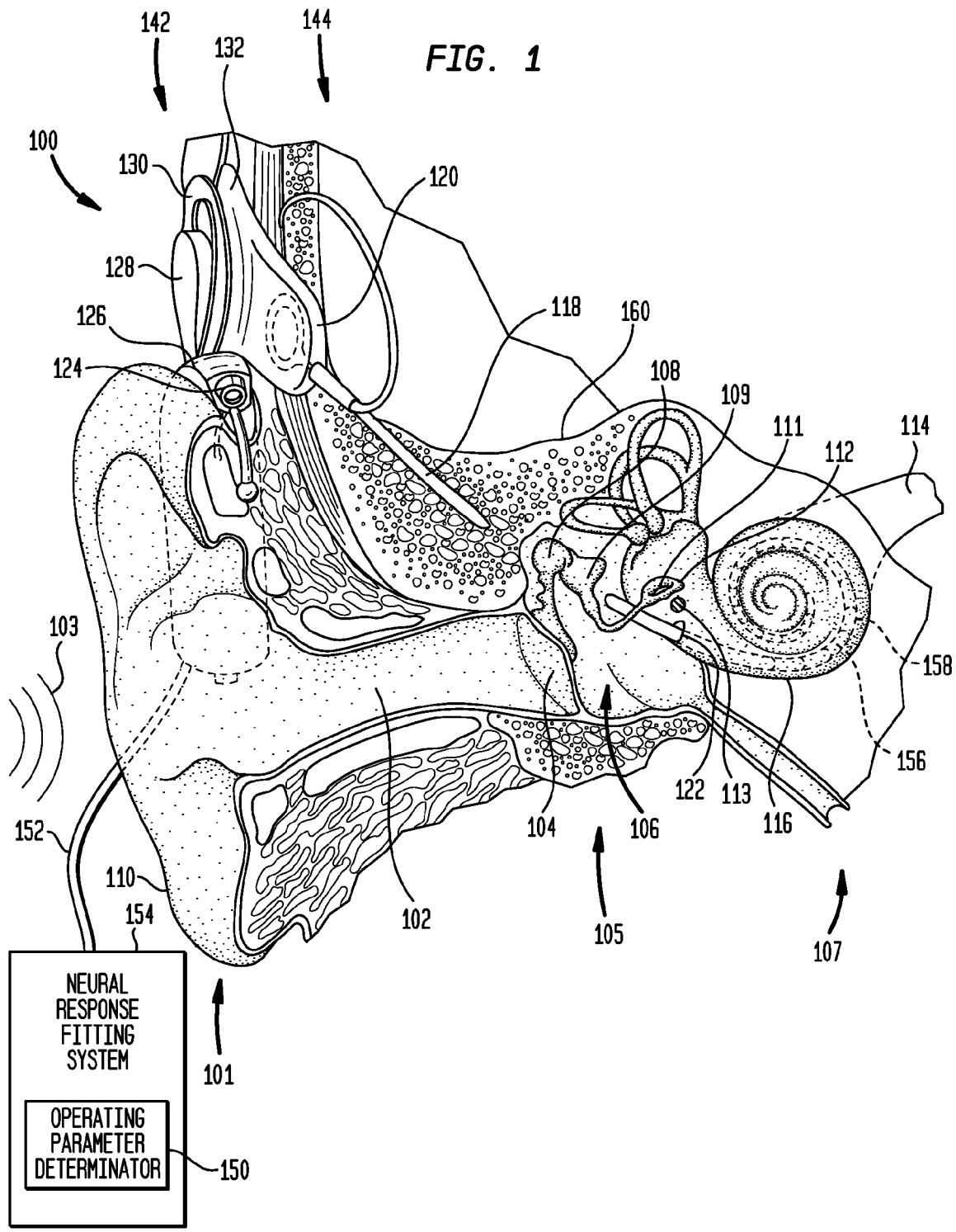
FIG. 1 is a perspective view of a cochlear implant fitting arrangement comprising a cochlear implant coupled to a neural response fitting system in which embodiments of the present invention may be advantageously implemented.

Referring to FIG. 1, the relevant components of outer ear 101, middle ear 105 and inner ear 107 are described next below. In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to acoustic wave 103. This vibration is coupled to oval window or fenestra ovalis 112 through three bones of middle ear 105, collectively referred to as the ossicles 106. The three bones comprising ossicles 106 are the malleus 108, the incus 109 and the stapes 111. Bones 108, 109 and 111 of middle ear 105 serve to filter and amplify acoustic wave 103, causing oval window 112 to articulate, or vibrate. Such vibration sets up waves of fluid motion within cochlea 116. Such fluid motion, in turn, activates tiny hair cells (not shown) that line the inside of cochlea 116. Activation of the hair cells causes appropriate nerve impulses to be transferred through the spiral ganglion cells and auditory nerve 114 to the brain (not shown), where they are perceived as sound.

Cochlear implant 100 comprises external component assembly 142 which is directly or indirectly attached to the body of the recipient, and an internal component assembly 144 which is temporarily or permanently implanted in the recipient. External assembly 142 typically comprises microphone 124 for detecting sound, a speech processing unit 126, a power source (not shown), and an external transmitter unit 128. External transmitter unit 128 comprises an external coil 130 and, preferably, a magnet (not shown) secured directly or indirectly to the external coil. Speech processing unit 126 processes the output of microphone 124 positioned, in the depicted embodiment, by auricle 110 of the recipient. Speech processing unit 126 generates coded signals, referred to herein as a stimulation data signals, which are provided to external transmitter unit 128 via a cable (not shown). Speech processing unit 126 is, in this illustration, constructed and arranged so that it can fit behind the outer ear 110. Alternative versions may be worn on the body or it may be possible to provide a fully implantable system which incorporates the speech processor and/or microphone into the implanted stimulator unit.

Internal components 144 comprise an internal coil 132, a stimulator unit 120, and an electrode assembly 118. Typically, a magnet (not shown) is fixed relative to internal coil 132. Internal coil 132 and stimulator unit 120 are hermetically sealed within a biocompatible housing. Internal coil 132 receives power and data from external coil 130, as noted above. Electrode assembly 118 extends from stimulator unit 120 to cochlea 116 through temporal bone 160. Electrode assembly 118 enters cochlea 116 via an opening of the perilymphatic spaces of cochlea 116, referred to as a cochleostomy 122. It should be appreciated that electrode assembly 118 may be implanted into cochlea 116 through another aperture in the cochlea. For example, rather than cochleostomy 122, electrode assembly 118 may be implanted via oval window 112, round window 113 or other natural or man-made aperture in cochlea 116. Electrode assembly 118 comprises an array 156 of electrodes 158 positioned to be substantially aligned with portions of tonotopically-mapped cochlea 116. Stimulation signals generated by stimulator unit 120 are applied by electrodes 158 to cochlea 116, thereby stimulating auditory nerve 114 to cause a hearing percept representative of the received sound 103.

In one embodiment, external coil 130 transmits electrical signals to internal coil 132 via a radio frequency (RF) link. The internal coil is typically a wire antenna coil comprised of one and preferably multiple turns of electrically insulated single-strand or multi-strand platinum or gold wire. The electrical insulation of internal coil 132 is provided by a flexible silicone molding (not shown). In use, implantable stimulator unit 120 may be positioned in a recess of the temporal bone adjacent auricle 110 of the recipient.

Further details of a conventional cochlear implant device may be found in U.S. Pat. Nos. 4,532,930, 6,537,200, 6,565,503, 6,575,894 and 6,697,674, which are hereby incorporated by reference herein.

Cochlear implant 100 is operationally coupled to a neural response fitting system 154 in which embodiments of the present invention may be implemented. As shown in FIG. 1, in one embodiment, neural response fitting system 154 is communicably coupled to speech processor 126 via a cable 152. As one of ordinary skill in the art would appreciate, however, fitting system 154 may be operationally and communicably coupled to cochlear implant 100 by any means now or later developed.

As noted, the effectiveness of a prosthetic hearing implant is dependent on the manner in which the device is customized to conform to the requirements for a particular recipient. This customization or "fitting" process involves the collection and determination of certain operating parameters such as the noted threshold and current levels. These and other recipient-specific operating parameters are relatively time consuming and/or difficult to measure in certain circumstances such as intra-operatively or when fitting the prosthetic hearing implant to a juvenile recipient.

As noted, aspects of the present invention are generally directed to the rapid and accurate derivation of operating parameters for each of a plurality of stimulation channels of a stimulating medical device. Generally, a recipient-specific operating parameter is directly measured for a selected subset of the stimulation channels. These measured values are then used to estimate, for example, via interpolation, the same operating parameter for at least some and perhaps all of the remaining stimulation channels. The accuracy of these estimated operating parameter values are then validated for each such stimulation channel. Accurate values are deemed valid and are retained while inaccurate estimated values are deemed invalid and are replaced with a new value that is either measured or re-estimated.

In one embodiment of the present invention, there is a one-to-one correspondence between a stimulation channel and an electrode 158 in electrode array 156. As one of ordinary skill in the art would appreciate, however, in other applications of a cochlear implant or other stimulating medical device, there may or may not be a one-to-one correspondence between stimulation channels and electrodes. As such, it should be appreciated that although throughout this specification the term "stimulation channel" may also be read as a reference to an individual electrode 158, the present invention is not so limited.

Figure 2:
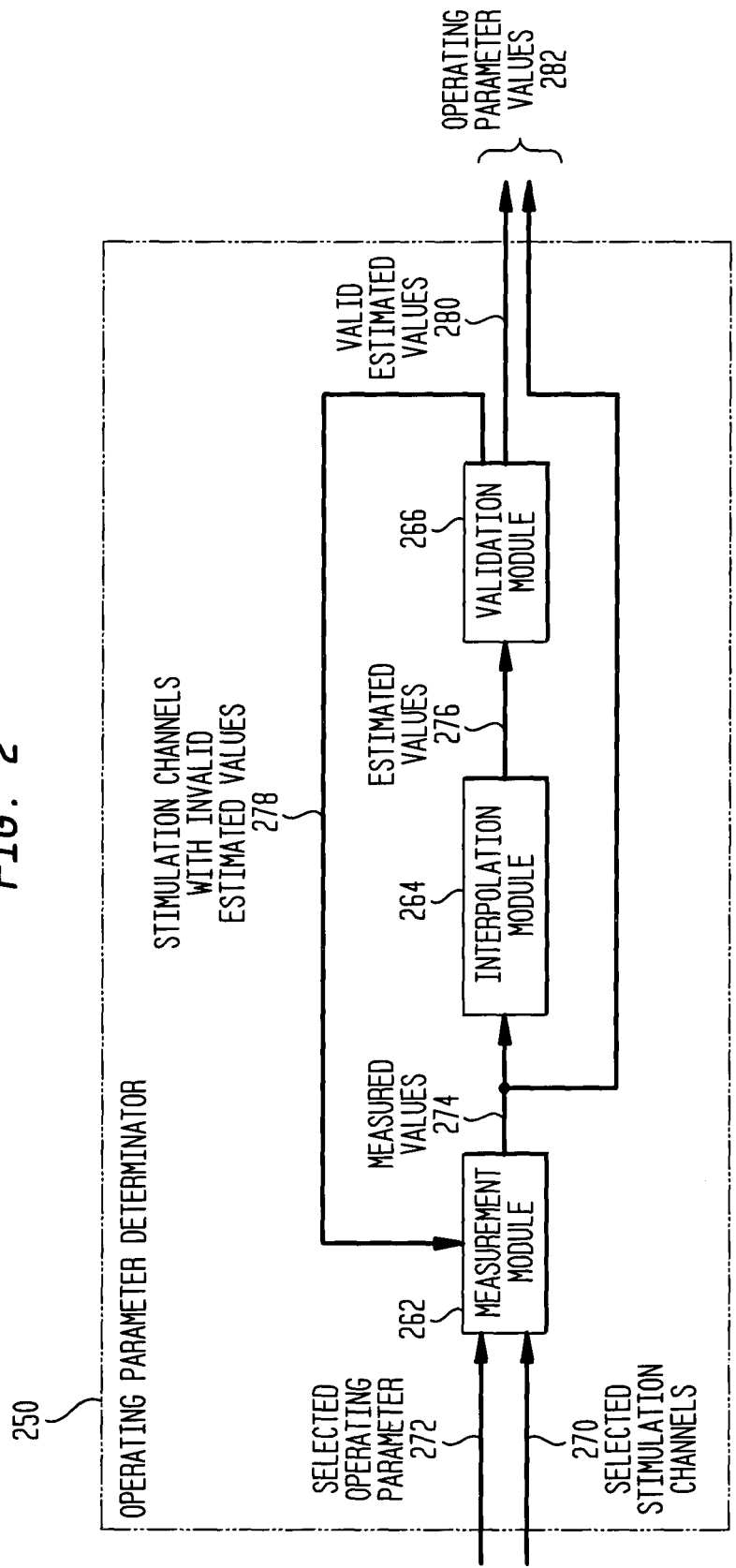
FIG. 2 is a functional block diagram of one embodiment of the operating parameter determinator illustrated in FIG. 1.

FIG. 2 is a functional block diagram of one embodiment of operating parameter determinator 150 of neural response fitting system 154 (FIG. 1), referred to herein as operating parameter determinator 250. Typically, fitting system 154 comprises one or more software programs executing on a processor-based system such as a personal computer, server, workstation or the like. In such environments, embodiments of operating parameter determinator 150 may comprise one or more software programs executing on one or more of the same or different processors executing in fitting system 154. Although the embodiments described herein are presented in such a context, it should be understood that determinator 150 may be implemented in any combination of hardware, software, firmware, etc. For example, in one embodiment, determinator 150 is implemented in an application specific integrated circuit, or ASIC.

It should also be appreciated that fitting system 154 may be distributed across more than one physical device. For example, in one alternative embodiment, the components of fitting system 154 which communicate with cochlear implant 100 are located in one location while the processing and/or user interface components of fitting system 154 are located in another location. Such components may transfer data and otherwise interoperate via any communication mechanisms now or later developed, including networks and the like.

With continued reference to FIG. 2, parameter determinator 250 comprises three primary functional components implemented in the same or different software programs or software modules executing on the same or different processors in fitting system 154: a measurement module 262, an interpolation module 264 and a validation module 266. The functions and operations performed by parameter determinator 250 and its component modules 262, 264, and 266 are described next below with reference to the flow charts illustrated in FIGS. 5A-5B and 6A-6B.

Because of the currently common usage of threshold and current levels, exemplary embodiments of the present invention are described herein in the context of determining the values of such operating parameters for cochlear implant 100. However, as one of ordinary skill in the art would appreciate, the present invention may be used to determine the values of any operating parameter for any stimulating medical device now or later developed.

Figure 5A:
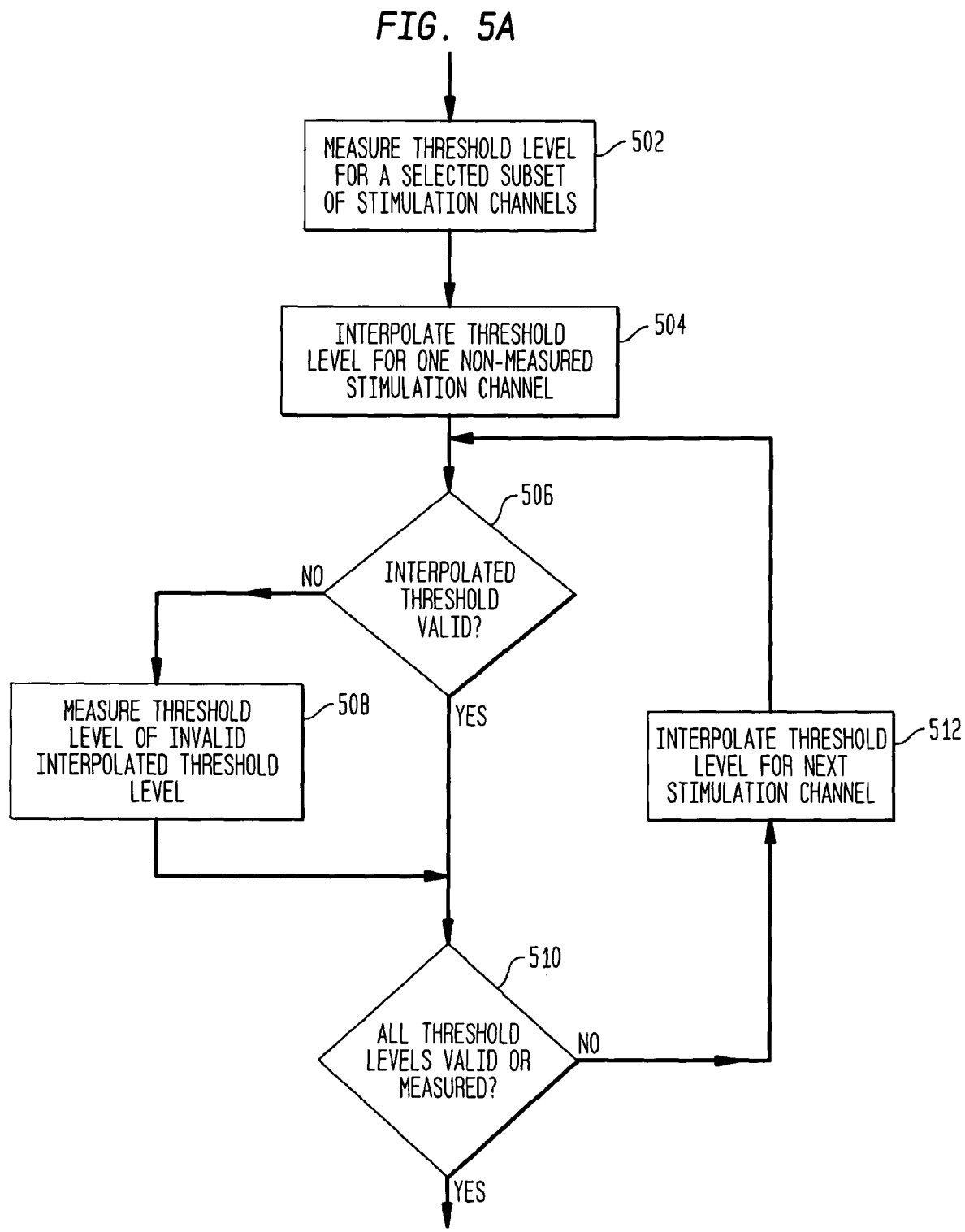
FIG. 5A is a flow chart of one embodiment of the operations performed to determine a recipient-specific operating parameter to fit to a particular recipient the cochlear implant illustrated in FIG. 1.
Figure 5B:
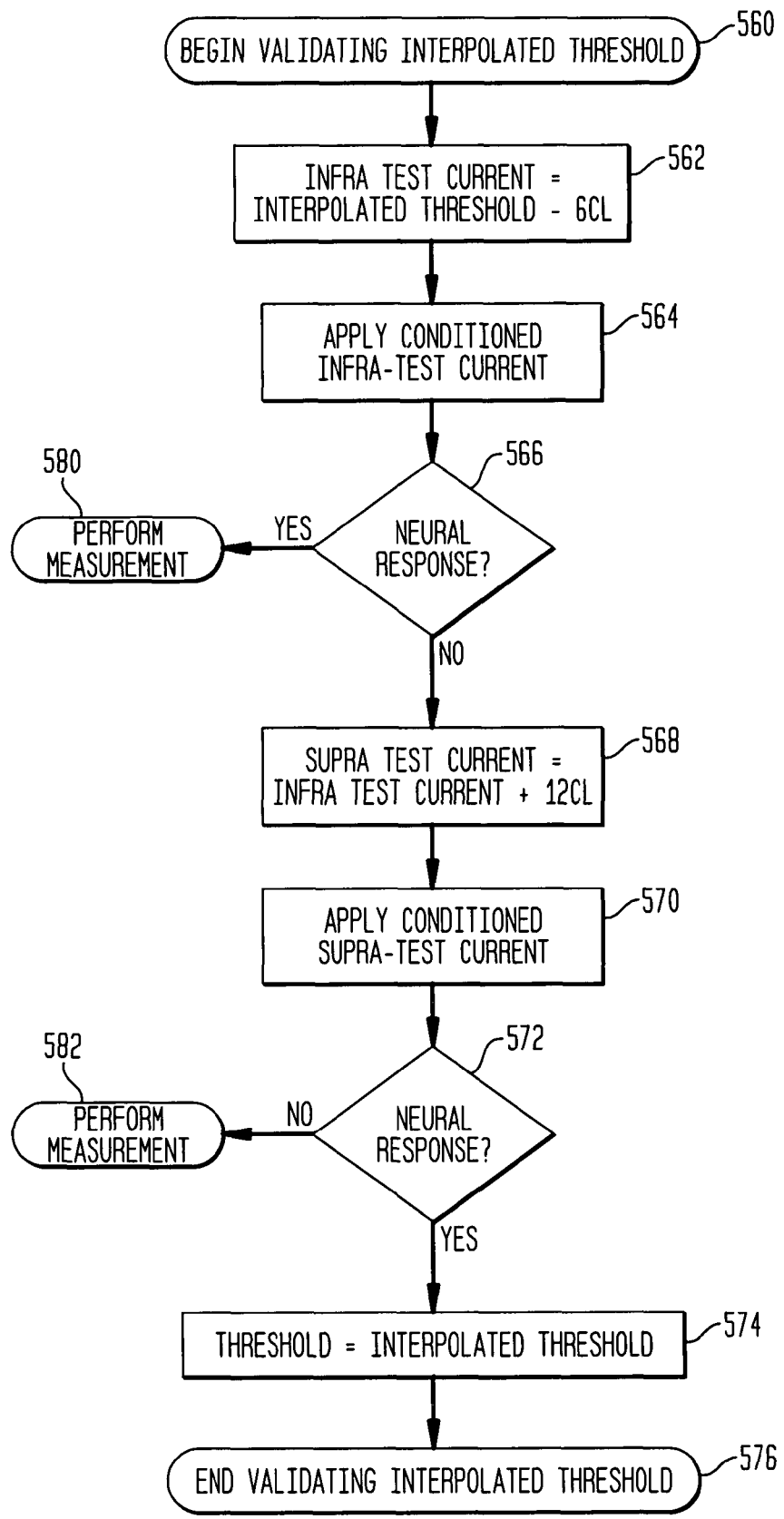
FIG. 5B is a flow chart of the operations performed to validate an estimated recipient-specific parameter in accordance with one embodiment of the present invention.

FIGS. 5A and 5B are flow charts of embodiments of the operations performed to determine a recipient-specific operating parameter to fit to a particular recipient the cochlear implant illustrated in FIG. 1. Measurement module 262 measures a selected operating parameter 272, here the recipient-specific operating parameter threshold level, for selected stimulation channels 270. This is referred to at block 502 in FIG. 5A. Measurement module 262 is not limited to implementing any specific type of measurement technique to measure selected operating parameter 272.

One proposed method of measuring recipient-specific operating parameters is to directly measure the response of auditory nerve 114 to an electrical stimulation. The direct measurement of neural responses, commonly referred to as Electrically-evoked Compound Action Potentials (ECAPs) in the context of cochlear implants, provides an objective measurement of the response of nerves to electrical stimulation. Following electrical stimulation, the neural response is caused by the superposition of single neural responses at the outside of the axon membranes. The measured neural response is transmitted to an externally-located system, typically via telemetry. Such Neural Response Telemetry NRT® (NRT is registered trademark of Cochlear Limited, Lane Cove, NSW, Australia) provides measurements of the ECAPs from within cochlea 116 in response to various stimulations. Measurements which are taken to determine whether a neural response or ECAPs has occurred are referred to herein as "NRT® measurements."

In a system using NRT®, the minimum stimulation current level required to evoke a neural response at a given electrode 158 is commonly referred to herein as the threshold NRT® level, or T-NRT. Generally, the neural response resulting from a stimulation presented at one electrode 158 is measured at an adjacent electrode, although this need not be the case.

Figure 3A:
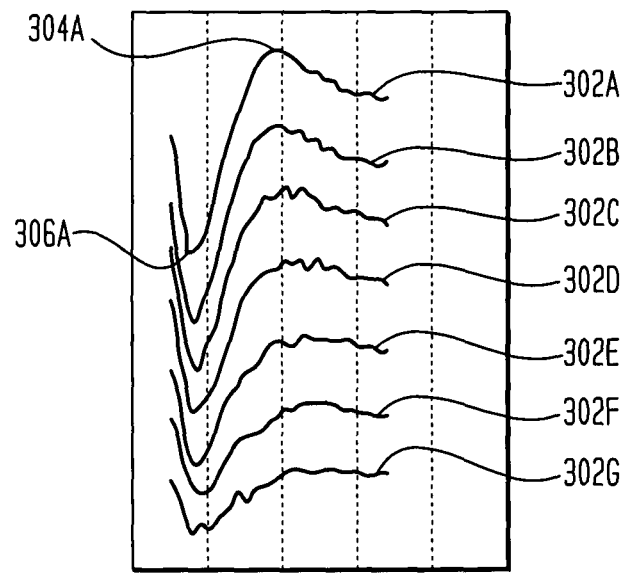
FIG. 3A is a graph illustrating exemplary measurements of sensed or measured obtained measured neural responses evoked by varying stimulation levels.

A sequence 300 of NRT® measurements 302 is shown in FIG. 3A. Sequence 300 contains seven NRT® measurements 302A-302G illustrating an acceptable neural response of a human auditory nerve 114. Each NRT® measurement waveform 302A-302G comprises a clear negative peak (N1) 304 and positive peak (P1) 306. (Only reference numerals 304A and 306A are depicted in FIG. 3A for clarity). As used herein, a "good" neural response is one which closely approximates a true neural response to an applied stimulation current.

An NRT® measurement waveform may have a partial N1 peak, no P1 peak or a double positive peak P1 and P2 and still represent a good neural response. The measurement waveforms 302 toward the top of the graph depicted in FIG. 3A (measurement waveforms 302A, 302B, for example) indicates a stronger neural response to a relatively large neural stimulation, while the measurement waveforms toward the bottom of the graph (measurement waveforms 302F and 302G, for example) indicate a weaker neural response with reduced stimulation.

Figure 3B:
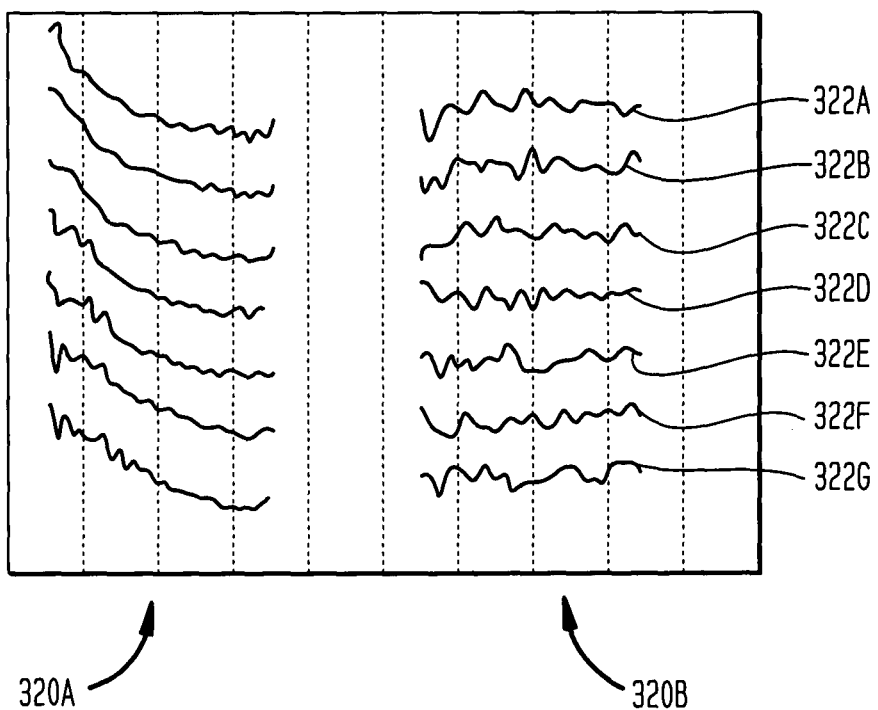
FIG. 3B is a graph illustrating exemplary measurements of sensed or measured neural response showing stimulation artifact and noise.

Two sequences 320A and 320B of the seven illustrated NRT® measurements 322A-322G that display the absence of a neural response are shown in FIG. 3B. In the left-hand sequence 320A, stimulation artifact and/or noise are observed. The stimulation artifact may give the impression of artificial peaks which may be interpreted as a neural response to a previously applied stimulation signal. In right-hand sequence 320B, noise is observed.

Distinguishing between measurements that display a neural response such as those of FIG. 3A, and measurements which do not display a neural response such as those of FIG. 3B, is an important aspect of performing NRT® measurements. This task may be difficult, for instance when the combination of stimulation artifact and noise gives the appearance of a weak neural response.

One conventional approach to determining T-NRT values is the Amplitude Growth Function (AGF) method. The AGF method is based on the premise that the peak-to-peak amplitude of a neural response increases linearly with stimulation current level. It should be appreciated, however, that the relationship is more accurately defined by a sigmoidal function. By obtaining the value at different stimulation current levels, a regression line may be drawn through these measurement points and extrapolated to the point at which the peak-to-peak amplitude becomes zero, thus indicating the threshold stimulation level.

Figure 4:
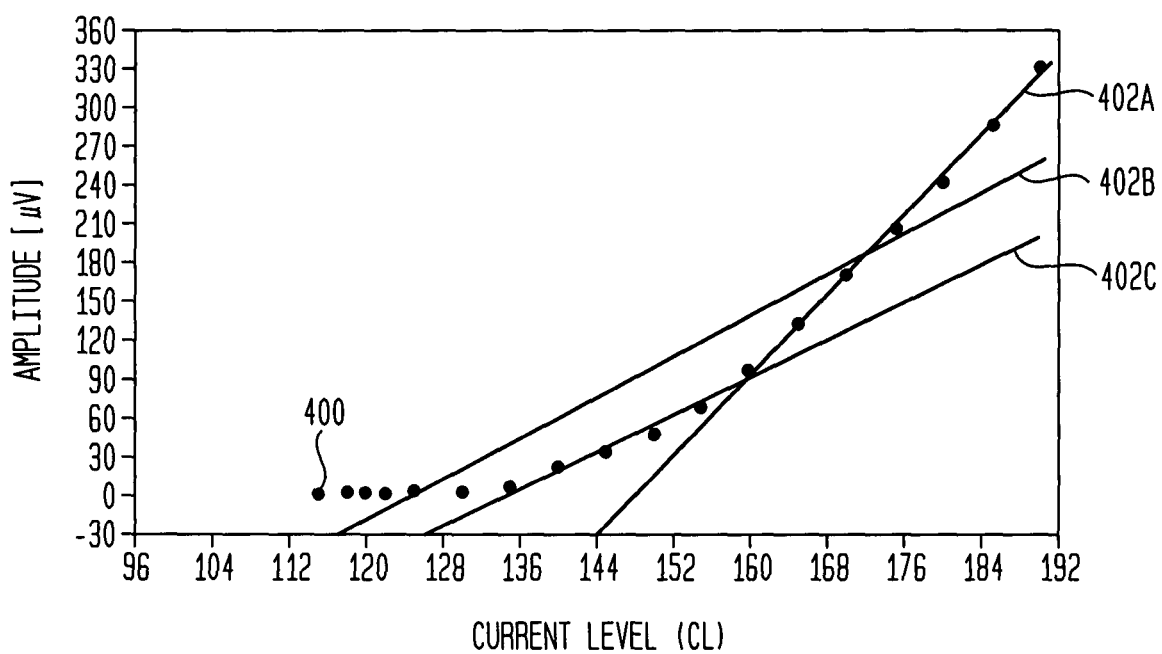
FIG. 4 is a graph of peak-to-peak evoked neural response amplitude vs. stimulation current level, showing possible regression lines.

For example, FIG. 4 illustrates a typical, non-linear, measurement set of peak-to-peak amplitude (in microvolts) vs. current level (in digitized current level units). In this illustrative example, there is a one-to-one exponential relationship between the unit of current level and the conventional unit of current (the ampere). In one example, the current level scale is from 0 to 255 with each unit representing an increasingly larger quantities of amperes. This single set of measurements 400 (only one of which is referenced in FIG. 4 for ease of illustration) can be fitted with a number of regression lines 402A, 402B and 402C, yielding possible T-NRT values of 125, 135 and 158 current level units, a variation of over 30 current levels. This is because the AGF is observer-dependent due to the observer selecting the measurement points to include in the regression analysis.

In addition, the AGF method requires a significant number of NRT® measurements above the threshold to enable a regression line to be determined. Such measurements may be beyond the recipient's loudest acceptable or comfort level, and thus the ability to post-operatively obtain such measurements is limited. Additionally, such measurements do not yield a simple linear relationship. This contributes to the potential plurality of regression lines, such as regression lines 402A-C, resulting in significantly different T-NRT® levels from a given measurement set.

Visual detection of T-NRT levels is a more fundamental conventional approach. NRT® measurements of increasing stimulation level are performed until the stimulation level at which a neural response is detected, at which point the T-NRT level is defined as the current stimulation level. Visual detection depends critically on the acuity of the observer to distinguish between neural responses and artifact or noise. It should be appreciated, however, that visual detection is also observer-dependent.

Further details of measurement techniques suitable for implementation in measurement module 262 are described in co-pending and commonly owned U.S. patent application Ser. No. 10/569,054, which is hereby incorporated by reference herein.

In another embodiment, measurement module 262 measures threshold levels for selected stimulation channels 270 by using verbal feedback from the recipient. In a still further embodiment, a recipient measures the threshold levels for a subset of the selected subset of stimulation channels 270 to determine subjective threshold levels without assistance.

In one embodiment, twenty-two (22) stimulation channels are provided in cochlear implant 100. Of these 22 stimulation channels, five (5) stimulation channels are selected 270 for input to measurement module 262 for measurement. Selected stimulation channels 270 are generally equally spaced across electrode array 156, although they need not be in alternative embodiments. As one of ordinary skill in the art would appreciate, any number of selected stimulation channels 270 having any appropriate spacing may be utilized in alternative embodiments of the present invention. For example, in one embodiment, measurement module 262 measures the threshold levels of two stimulation channels to be delivered by electrodes 158 at opposing ends of electrode array 256, and three stimulation channels corresponding to electrodes 158 spaced evenly across electrode array 156. As one of ordinary skill in the art would appreciate, there are a myriad of other combinations of stimulation channels which may be measured by measurement module 262 to provide measured values 274 suitable to enable interpolation module 264 (described next below) to generate accurate estimated values 276 for selected operating parameter 272.

Interpolation module 264 estimates the values of selected operating parameter 272 for one or more, and preferably all, stimulation channels other than selected stimulation channels 270. In one embodiment, the threshold level for one non-measured stimulation channel is interpolated. In this example, the threshold level for the non-measured stimulation channel is interpolated using the measured threshold levels 274 from the nearest stimulation channels 270; that is, those that have been measured by measurement module 262 at block 502. This is depicted in block 504 of FIG. 5A.

Any interpolation technique may be used to determine the interpolated threshold levels (INT-T). Furthermore, the quantity of measured threshold levels that may be used in the interpolation is that which is appropriate for the implemented interpolation technique. In one embodiment, linear interpolation is utilized to determine estimated values 276. In one particular embodiment, linear interpolation as described in commonly owned U.S. patent application Ser. Nos. 10/569,054 and 10/518,812, the contents of which are hereby incorporated by reference herein, is utilized. It should be appreciated by those of ordinary skill in the art that other forms of interpolation may be implemented in alternative embodiments of the present invention. Such interpolation approaches include, but are not limited to, polynomial interpolation, spline interpolation, rational interpolation, and trigonometric interpolation.

Estimated value 276 for selected operating parameter 272 for the non-selected stimulation channels is then validated by validation module 266. This is depicted in block 506 of FIG. 5A. One embodiment of the operations performed by validation module 266 at block 506 is described next below with reference to FIG. 5B.

Referring to FIG. 5B, the validation process begins at block 560. At block 562, the current level (CL) that will be applied to an electrode of interest, referred to herein as the infra-test current level, is set equal to the interpolated threshold level (INT-T) minus some predetermined current level. In one embodiment, that current level is 6 CLs, although other current levels may be subtracted from an interpolated threshold to attain the infra-test current.

At block 564 the infra-test current is conditioned and applied to the electrode 158 of interest. In one embodiment, validation module 266 implements a technique that removes or minimizes stimulation artifacts, prevents clipping, and optimizes the stimulation to be applied. Details of such operations are described in U.S. patent application Ser. No. 10/569,054, which is hereby incorporated by reference herein.

After application of the infra-test stimulation current at block 564, invalidation module 266 determines whether the applied stimulation has induced a neural response at block 566. In one embodiment, a recipient may provide feedback to determine if a neural response has been induced. In another embodiment, a machine learned expert system is used to determine if a neural response has occurred. In another embodiment, at block 566 a machine-learned expert system is utilized to predict whether an NRT measurement contains a neural response based on the plurality of extracted auditory signal features. In one embodiment, the expert system utilizes induction of decision trees to make such a determination. In one particular implementation of such an embodiment, the induction of decision trees machine learning algorithm is the algorithm C5.0 described in Quinlan, J., 1993. "C4.5: Programs for Machine Learning." Morgan Kaufmann, San Mateo; and Quinlan, J., 2004. "See5: An Informal Tutorial." Rulequest Research, all of which are hereby incorporated by reference herein.

Figure 6A:
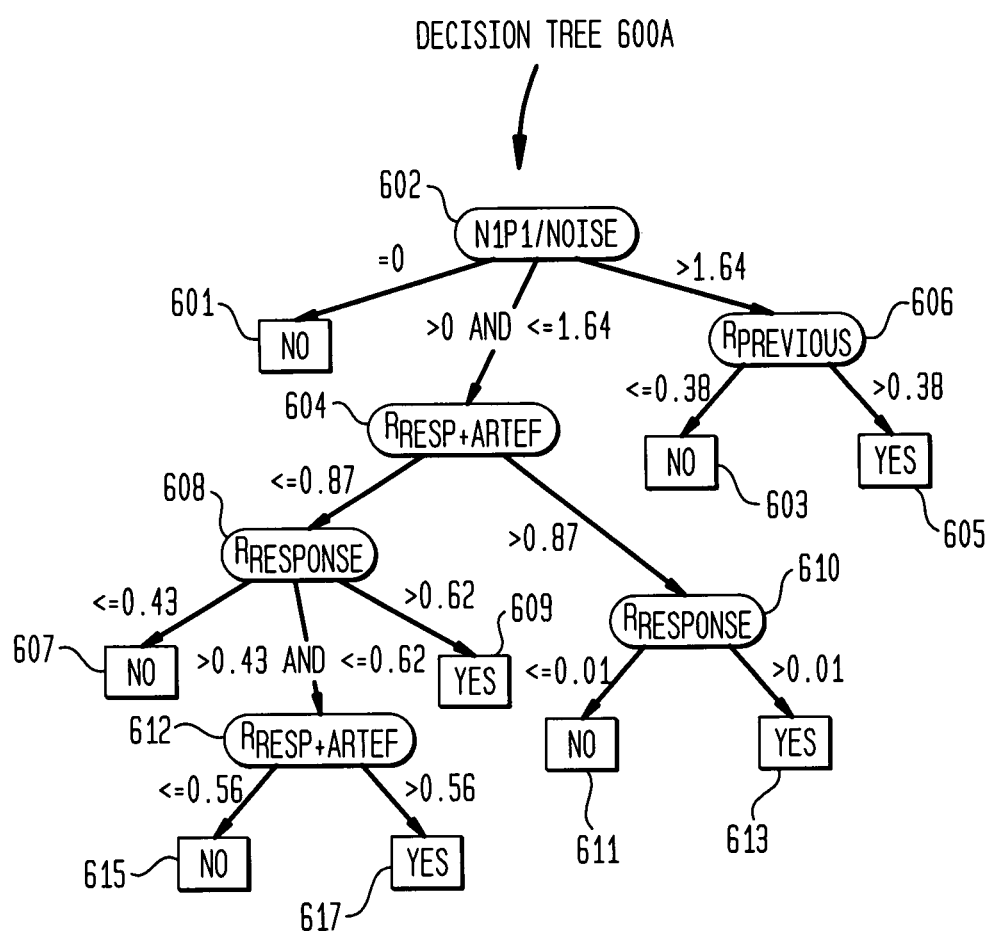
FIG. 6A illustrates one embodiment of a decision tree used in an embodiment of FIG. 4C to determine whether a neural response has been evoked.
Figure 6B:
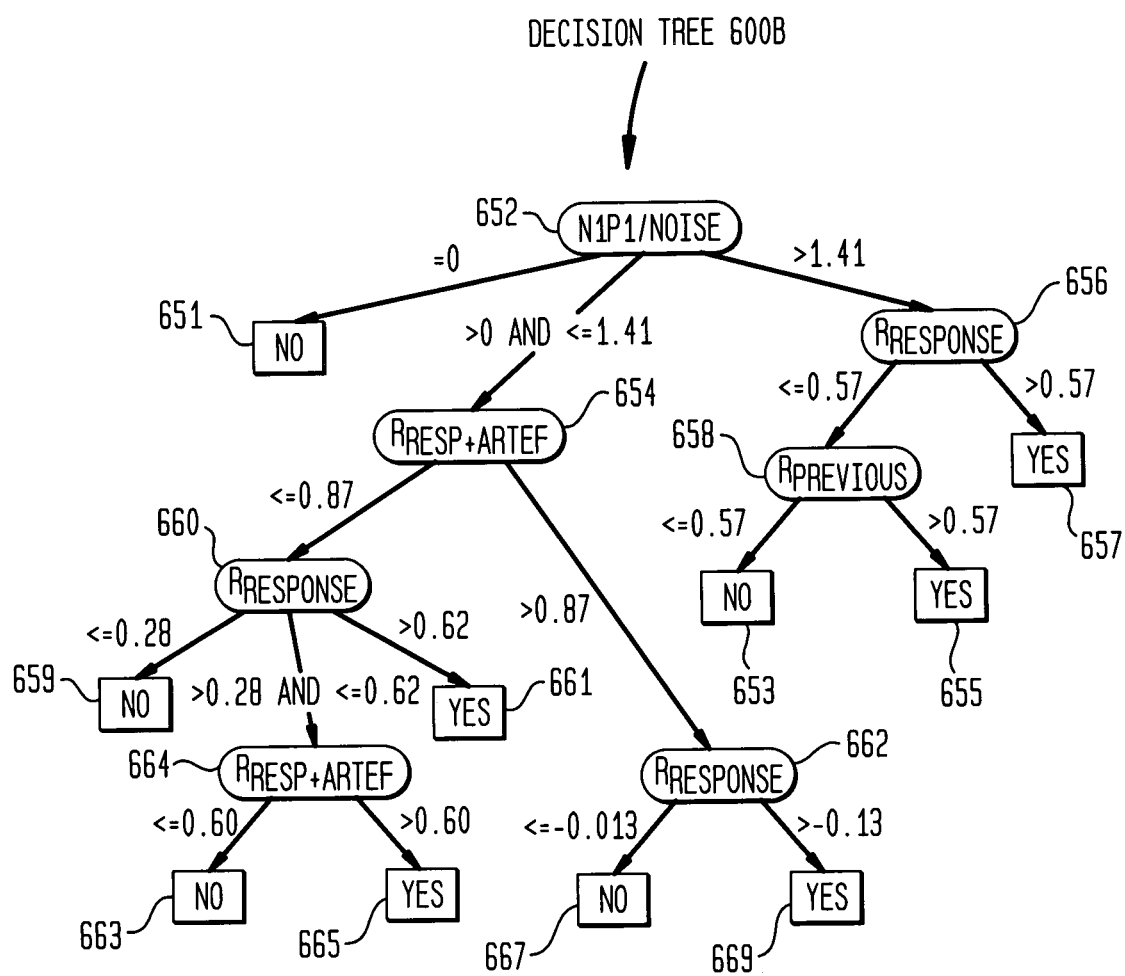
FIG. 6B illustrates another embodiment of a decision tree used in one embodiment of FIG. 5B to determine whether a neural response has been evoked.

Two embodiments of a decision tree which may be implemented by a neural response expert system are illustrated in FIGS. 6A and 6B. Decision tree 600A (FIG. 6A) may be configured to minimize the occurrence of false positive events while decision tree 600B (FIG. 6B) may be configured to minimize the overall error rate as compared to decision tree 600A. The utilization of two such decision trees 600A and 600B to determine T-NRT is advantageous is some applications. For example, in embodiments in which the stimulation current level is incrementally increased, decision tree 600A may be utilized to provide a low false-positive rate so that a neural response can be predicted with a high degree of confidence. Alternatively, in embodiments in which the stimulation current level is incrementally decreased, decision tree 600B may be utilized due to its ability to more accurately predict a neural response has occurred.

In one embodiment, the decision tree 600A illustrated in FIG. 6A is applied to the obtained 32 sample set measurement of the NRT measurement. That is, validation module 266 implements a neural response expert system that considers or processes a plurality of features extracted from the NRT measurement to determine if it contains a "good" neural response. As noted, a "good" neural response is one which approximates a true neural response to the applied stimulus level as determined by a sampling a statistically-significant population of recipients.

Should decision tree 600A determine that a given NRT measurement does not contain a "good" neural response and thus that a neural response has not been evoked (block 566), the process continues at block 568, described below, at which the stimulus current level CL is incrementally increased.

Referring now to FIG. 6A, each parameter considered in decision tree structure or dichotomous key 600A is defined herein below. As one of ordinary skill in the art would appreciate, the use of the terms attributes, parameters, features and the like are commonly used interchangeably to refer to the raw and calculated values utilized in a decision tree. The selection of such terms herein, then, is solely to facilitate understanding. It should also be appreciated that the first occurring peak positive and negative values of an NRT measurement waveform are commonly referred to as P1 and N1, respectively, as noted above. For ease of description, these terms are utilized below. In the following description, the attributes considered at each of the decision nodes 602, 604, 606, 608, 610 and 612 are first described followed by a description of decision tree 600A.

Attribute N1P1/Noise is considered at decision node 602. Attribute N1P1/Noise represents the signal to noise ratio of the NRT measurement. As noted, in the exemplary embodiment, each NRT measurement provides a trace or waveform derived from 32 samples of the neural response obtained at a sampling rate of 20 kHz.

N1 is the minimum of the first 8 samples.
P1 is the maximum of the samples after N1, up to and including sample 16.
N1−P1 (µV)=ECAP$_{P1}$−ECAP$_{N1}$.
If any of the following rules are true, N1−P1=0:
N1−P1<0
Latency between N1 and P1<2 samples
Latency between N1 and P1>12 samples
Latency between N1 and the maximum sample post-N1>15 samples AND Ratio of N1−P1 to the range N1 onwards <0.85
Noise=the range (maximum minus minimum) of samples 17-32.
N1P1/Noise=N1−P1 (amplitude) divided by Noise (the noise level).

Figure 7:
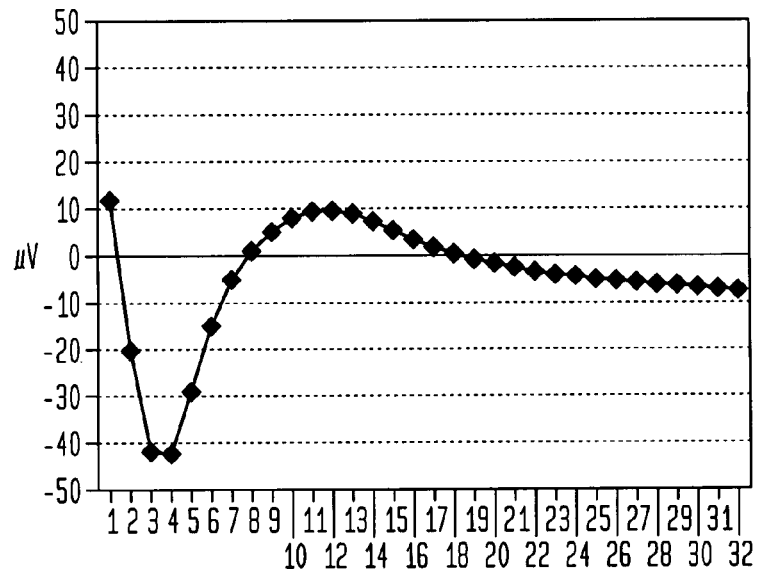
FIG. 7 is a graph illustrating a predefined expected or 'good' neural response used for comparison by a portion of the decision trees of FIGS. 6A and 6B.

Attribute R$_{Response}$ is considered at decision nodes 608 and 610. Attribute R$_{Response}$ is defined as the correlation coefficient between the given NRT measurement and a fixed good response, calculated over samples 1-24. A predefined 32 sample standard response used in the present embodiment is shown in FIG. 7. In this embodiment, the standard correlation coefficient is utilized:

$$r = \frac{\sum_{Samples}(x-\bar{x})(y-\bar{y})}{\sqrt{\sum_{Samples}(x-\bar{x})^2 \sum_{Samples}(y-\bar{y})^2}}$$

Figure 8:
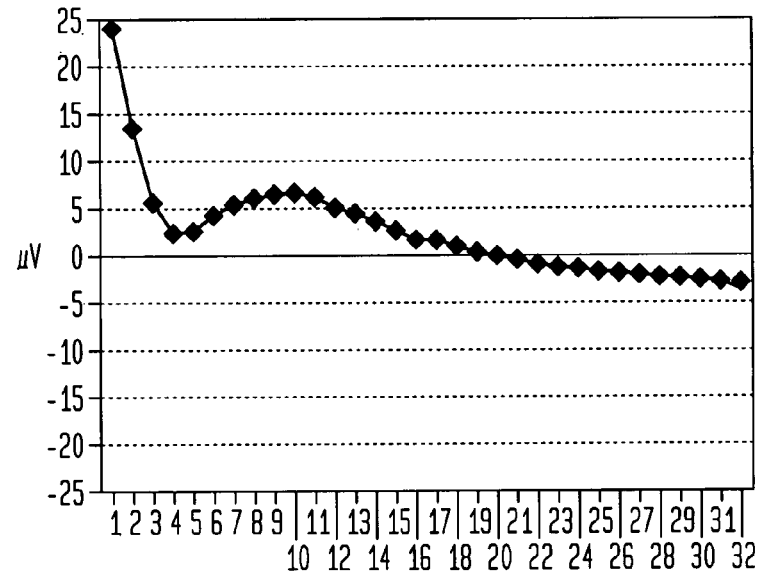
FIG. 8 is a graph illustrating a predefined expected or 'good' neural response plus stimulus artifact used for comparison by a portion of the decision trees of FIGS. 6A and 6B.
Figure 9:
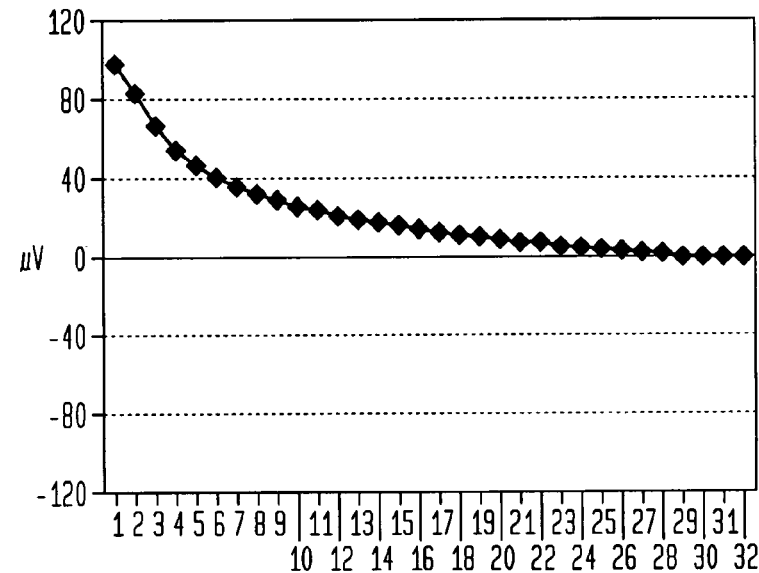
FIG. 9 illustrates a predefined expected or 'good' stimulus artifact.

Attribute R$_{Resp+Artef}$ is considered a decision nodes 604 and 612. Attribute R$_{Resp+Artef}$ is defined as the correlation coefficient between the given NRT measurement and a fixed trace with neural response plus artifact, calculated over samples 1-24. FIG. 8 is a graph illustrating a predefined expected or 'good' neural response plus stimulus artifact. FIG. 9 illustrates the stimulus artifact.

Attribute R$_{Previous}$ is considered a decision node 606. Attribute R$_{Previous}$ is defined as the correlation coefficient between the given NRT measurement and the NRT measurement of immediately lower stimulus current level, calculated over samples 1-24. In one embodiment, any previously performed measurement of lower stimulus level, whether the step difference is 2CL, 6CL, etc.

As shown in FIG. 6A, when N1P1/Noise is zero, decision tree 600A predicts that the NRT measurement does not contain a neural response as illustrated by decision node 601. Should N1P1/Noise 602 have a value between 0.0 and 1.64, then the value of attribute $R_{Resp+Artef}$ is considered at decision node 604. Similarly, should N1P1/Noise have a value greater than 1.64, then the value of attribute $R_{Previous}$ is considered at decision node 606.

At decision node 604 of attribute $R_{Resp+Artef}$ is considered. If it determined to be less than or equal to 0.87, then attribute $R_{Response}$ is determined at decision node 608. However, if attribute $R_{Resp+Artef}$ is determined to be greater than 0.87, then a different consideration of attribute $R_{Response}$ is performed at decision node 610.

Returning to decision node 606 at which attribute $R_{Previous}$ is considered. If the attribute is less than or equal to 0.38, then decision tree 600A determines that the given NRT measurement fails to contain a neural response, as indicated at block 603 of FIG. 6A. However, if the attribute is greater than 0.38, then decision tree 600A determines that the given NRT measurement does contain a neural response, as indicated at block 605 of FIG. 6A. Thus, if the attribute N1P1/Noise is greater than 1.64 and the attribute $R_{Previous}$ is greater than 0.38, then the NRT measurement is predicted to contain a neural response.

At decision node 608 decision tree 600A considered whether attribute $R_{Response}$ is less than or equal to 0.43, in which case decision tree 600A predicts that the NRT measurement does not contain a neural response, as shown at block 607. At decision node 608 decision tree 600A also considers whether attribute $R_{Response}$ is greater than 0.62, at which decision tree 600A predicts that the NRT measurement does contain a neural response, as shown at block 609. Thus, if the attribute N1P1/Noise is greater than zero and less than or equal to 1.64, attribute $R_{Resp+Artef}$ is less than or equal to 0.87 and attribute $R_{Response}$ is less than 0.62, then decision tree 600A predicts that the NRT measurement contains a neural response.

At decision node 610 decision tree 600A considered whether attribute $R_{Response}$ is less than or equal to 0.01, in which case decision tree 600A predicts that the NRT measurement does not contain a neural response, as shown at block 611. At decision node 610 decision tree 600A also considers whether attribute $R_{Response}$ is greater than 0.01, at which decision tree 600A predicts that the NRT measurement does contain a neural response, as shown at block 613. Thus, if the attribute N1P1/Noise is greater than zero and less than or equal to 1.64, parameter $R_{Resp+Artef}$ is greater than 0.87, and attribute $R_{Response}$ is greater than 0.01, then decision tree 600A predicts that the NRT measurement contains a neural response.

Returning to decision node 608, decision tree 600A also considers whether attribute $R_{Response}$ is greater than 0.43 and less than or equal to 0.62. If so, decision tree 600A considers attribute $R_{Resp+Artef}$ at decision node 612. There, if $R_{Resp+Artef}$ is less than or equal to 0.56, then decision tree 600A predicts that the NRT measurement does not contain a neural response, as indicated at block 615. Alternatively, if $R_{Resp+Artef}$ is greater than 0.56, then decision tree 600A predicts that the NRT measurement contain a neural response, as indicated at block 617. Thus, if the attribute N1P1/Noise is greater than zero and less than or equal to 1.64, parameter $R_{Resp+Artef}$ is less than or equal to 0.87, attribute $R_{Response}$ is greater than 0.43 and less than or equal to 0.62, and attribute $R_{Resp+Artef}$ is greater than 0.56, then decision tree 600A predicts that the NRT measurement contains a neural response.

As one or ordinary skill in the art would appreciate, the above values are exemplary only. For example, in one alternative embodiment, N1 is determined based on a quantity of sampled other than eight. Similarly, the positive peak occurs after the negative peak in NRT measurement waveforms. In the above embodiment, the positive peak is limited to the maximum sample after the first occurring negative peak N1. However, the trailing portion of an NRT waveform is generally level and should not contain a pulse. It should be appreciated, however, that in alternative embodiments, P1 is defined as the maximum sample which occurs after N1 and less than 14-18 samples. Similarly, the latency between the first occurring negative and positive peaks may be other than 2 and 12 samples in alternative embodiments.

Referring now to FIG. 6B, decision tree 600B will be described. The attributes considered or evaluated at decision blocks 652, 654, 656, 658, 660, 662 and 664 are described above.

At decision node 652 attribute N1P1/Noise is considered by decision tree 600B. If the attribute N1P1/Noise zero, decision tree 600B predicts that the NRT measurement does not contain a neural response as illustrated by decision node 651. Should the attribute N1P1/Noise have a value greater than 0.0 and less than or equal to 1.41, then the value of attribute $R_{Resp+Artef}$ is considered at decision node 654. Similarly, should the attribute N1P1/Noise have a value greater than 1.41, then the value of attribute $R_{Response}$ is considered at decision node 656.

At decision node 654, attribute $R_{Resp+Artef}$ is considered. If this attribute is determined to be less than or equal to 0.87, then attribute $R_{Response}$ is considered at decision node 660. However, if attribute $R_{Resp+Artef}$ is determined to be greater than 0.87, then a different consideration of attribute $R_{Response}$ is performed at decision node 662.

Returning to decision node 656 at which attribute $R_{Response}$ is considered. If the attribute is less than or equal to 0.57, then decision tree 600B considers the attribute $R_{Previous}$ at decision node 658. However, if the attribute $R_{Previous}$ is greater than 0.57, then decision tree 600B determines that the given NRT measurement contains a neural response, as indicated at block 657 of FIG. 6B. Thus, if the attribute N1P1/Noise is greater than 1.41 and the attribute $R_{response}$ is greater than 0.57, then the NRT measurement is predicted to contain a neural response.

Returning to decision node 658 at which attribute $R_{Previous}$ is considered. If this attribute is less than or equal to 0.57, then decision tree 600B determines that the given NRT measurement fails to contain a neural response, as indicated at block 663 of FIG. 6B. However, if this attribute is greater than 0.57, then decision tree 600B determines that the given NRT measurement does contain a neural response, as indicated at block 655 of FIG. 6B. Thus, if the attribute N1P1/Noise is greater than 1.41, the attribute $R_{Response}$ is less than or equal to 0.57, and the attribute $R_{Previous}$ is greater than 0.57, then the NRT measurement is predicted to contain a neural response.

At decision node 660 decision tree 600B considered whether attribute $R_{Response}$ is less than or equal to 0.28, in which case decision tree 600B predicts that the NRT measurement does not contain a neural response, as shown at block 659. At decision node 608 decision tree 600B also considers whether attribute $R_{Response}$ is greater than 0.62, in which case decision tree 600B predicts that the NRT measurement does contain a neural response, as shown at block 661. Thus, if the attribute N1P1/Noise is greater than zero and less than or equal to 1.41, attribute $R_{Resp+Artef}$ is less than or equal to 0.87, and attribute $R_{Response}$ is greater than 0.62, then decision tree 600B predicts that the NRT measurement contains a neural response.

At decision node 662 decision tree 600B considered whether attribute $R_{Response}$ is less than or equal to 0.013, in which case decision tree 600B predicts that the NRT measurement does not contain a neural response, as shown at block 667. At decision node 662 decision tree 600B also considers whether attribute $R_{Response}$ is greater than 0.013, in which case decision tree 600B predicts that the NRT measurement does contain a neural response, as shown at block 669. Thus, if the attribute N1P1/Noise is greater than zero and less than or equal to 1.41, attribute $R_{Resp+Artef}$ is greater than 0.87, and attribute $R_{Response}$ is greater than 0.013, then decision tree 600B predicts that the NRT measurement contains a neural response.

Returning to decision node 660, decision tree 600B also considers whether attribute $R_{Response}$ is greater than 0.43 and less than or equal to 0.62. If so, decision tree 600B considers attribute $R_{Resp+Artef}$ at decision node 664. There, if the attribute $R_{Resp+Artef}$ is less than or equal to 0.60, then decision tree 600B predicts that the NRT measurement does not contain a neural response, as indicated at block 663. Alternatively, if attribute $R_{Resp+Artef}$ is greater than 0.60, then decision tree 600B predicts that the NRT measurement contains a neural response, as indicated at block 665. Thus, if the attribute N1P1/Noise is greater than zero and less than or equal to 1.41, attribute $R_{Resp+Artef}$ is less than or equal to 0.87, attribute $R_{Response}$ is greater than 0.28 and less than or equal to 0.62, and attribute $R_{Resp+Artef}$ is greater than 0.60, then decision tree 600B predicts that the NRT measurement contains a neural response.

Further details of expert systems using decision trees are described in detail in U.S. patent application Ser. No. 10/569,054, which is hereby incorporated by reference herein.

As one or ordinary skill in the art would appreciate, the above values are exemplary only, and that other decision trees with other attributes and decision values may be implemented. It should also be apparent to one of ordinary skill in the art that other approaches may be implemented in validation module 266 to validate an interpolated threshold level. For example, in one embodiment, a less accurate expert system than that used to validate conventional objective measurements may be implemented in validation module 266.

Returning to FIG. 5B, at block 566 the interpolated threshold levels are either determined to be accurate; that is, valid, or inaccurate; that is, invalid. Accuracy is determined by whether a neural response has been detected in response to the application of the infra-test stimulation current since the infra-test stimulation current is lower than the interpolated value. If a response is detected, then the infra-test current level is determined to be too high and, therefore an invalid threshold level. In response to this determination, the actual threshold level is measured as indicated at block 580 of FIG. 5B. As one of ordinary skill in the art would appreciate, such a determination is based on the difference between the selected infra-test stimulation current and the interpolated value. It should also be appreciated that the infra-test stimulation current may be selected to attain a desired tradeoff of speed and accuracy, of the operation performed by validation module 266.

If there is no detected neural response at block 566, then the current level is increased to a supra-test current level. This value is attained by adding a predetermined current level to the infra-test current level or the initial interpolated value. In one exemplary embodiment, a delta current level of twice the current level that was subtracted from the initial interpolated value to arrive at the infra-test current level is added to the infra-test current level. This results in the infra-test and supra-test current levels being the same delta below and above, respectively, the initial interpolated value. In the example introduced above, the supra-test current level applied to an electrode of interest is set equal the previously applied current level of INT-T minus 6 CL plus 12 CL, or INT-T plus 6 CL. Thus, the new current level to be applied is a supra-threshold current level 6 CL above the interpolated T-NRT.

At block 570 validation module 266 applies and optimizes the current to be applied as described above in relation to block 564. It should be appreciated that in alternative embodiments, a different current level may be added to the infra-test current level or initial interpolated threshold value to attain a supra-test threshold level.

At block 572, it is determined whether the applied stimulation has evoked a neural response. This determination is performed in a manner that is the same or similar to that described above in relation to block 566. However, if at block 572 it has been determined that there is an absence of neural response, or an inaudible response, the threshold level is measured at block 582. However, if at block 572 the system detects a response, the validation module 366 sets the interpolated threshold (INT-T) to be the threshold level for the stimulation channel and terminates the validation process at block 576.

Returning to FIG. 5A, in one embodiment, a validation process such as that described above is, as noted, performed at block 506 for one non-measured stimulation channel. If the interpolated threshold value is determined to be inaccurate, then the threshold level is measured at block 508. On the other had, if the interpolated threshold level is determined to be valid (accurate), and the threshold level of other non-measured stimulation channels have not yet been validated (block 510), then operations proceed to block 512 at which the threshold level value for the next stimulation channel is determined and the operations beginning at block 506 are repeated. Otherwise, the process illustrated in FIG. 5A terminates when the threshold levels for all non-measured stimulation channels are validated at block 510.

It should be noted that although the present invention has been described with reference to Neural Response Telemetry (NRT®), it would be apparent to one of ordinary skill in the art that embodiments of the present invention may also be applied to other measures such as Electrically evoked Brainstem Audiometry (EABR), Electrically Evoked Stapedius Reflex Threshold (ESRT), Cortical evoked Potentials (CEP), or other measures known or used in the art today or in the future. Similarly, although the present invention has been described with reference to determining threshold levels, it would be apparent to one of ordinary skill in the art that the invention may be used to determine other target levels such as the comfort level as well as other levels known or used in the art. It should also be appreciated that embodiments of the present invention may be implemented in environments in which the threshold levels are not objectively measured; that is, where the thresholds are determined based on recipient's subjective feedback during a fitting process.

In one embodiment, the present invention is implemented using clinical and electrophysiological software. In alternative embodiments, the present invention is implemented in software, hardware or combination thereof.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any discussion of documents, acts, materials, devices, articles or the like which has been included in the present specification is solely for the purpose of providing a context for the present invention. It is not to be taken as an admission that any of these matters form part of the prior art or were common general knowledge in the field relevant to the present invention as it existed before the priority date of each claim of this application.

What is claimed is:

1. An apparatus constructed and arranged to determine operating parameter values for each of a plurality of stimulation channels of a cochlear implant, the apparatus comprising:
   a measurement module configured to objectively measure values of the operating parameter for selected stimulation channels of the cochlear implant;
   an interpolation module configured to interpolate the measured values to derive an estimated value of the operating parameter for one or more non-selected stimulation channels of the cochlear implant; and
   a validation module configured to assess the accuracy of each estimated value by:
      determining an infra-test value and a supra-test value of the operating parameter that is less than and greater than the estimated value, respectively;
      applying stimulation to the cochlear implant based on the infra-test and supra-test values, respectively; and
      determining the estimated value to be accurate if the infra-test value does not whereas the supra-test value does elicit a neural response, respectively.

2. The apparatus of claim 1, wherein the apparatus is further configured to retain each estimated value determined to be accurate.

3. The apparatus of claim 1, wherein, for each estimated value determined as inaccurate by the validation module, the measurement module is further configured to measure a new value of the operating parameter and to replace the estimated value with the new value.

4. The apparatus of claim 1, wherein the operating parameter comprises a recipient-specific operating parameter.

5. The apparatus of claim 4, wherein the recipient-specific operating parameter comprises:
   a minimum stimulation current level required to evoke a neural response at a given stimulation channel.

6. The apparatus of claim 4, wherein the recipient-specific operating parameter comprises:
   a stimulation level at which a sound is loud but comfortable to the recipient for each stimulation channel.

7. The apparatus of claim 1, wherein, for a given estimated value, the validation module is further configured to:
   determine the infra-test value by subtracting a desired value from the estimated value; and
   determine the supra-test value by adding the desired value to the estimated value.

8. An apparatus constructed and arranged to determine operating parameter values for each of a plurality of stimulation channels of a cochlear implant, comprising:
   means for objectively measuring the value of the operating parameter for at least a first stimulation channel and a second stimulation channel;
   means for estimating the value of the operating parameter for a third stimulation channel using the measured operating parameter values for the first and second stimulation channels; and
   means for assessing the accuracy of the estimated value of the operating parameter by:
      determining an infra-test value and a supra-test value of the operating parameter that is less than and greater than the estimated value, respectively;
      applying stimulation to the cochlear implant based on the infra-test and supra-test values, respectively; and
      determining the estimated value to be accurate if the infra-test value does not whereas the supra-test value does elicit a neural response, respectively.

9. The apparatus of claim 8, further comprising:
   means for retaining each estimated value determined to be accurate; and
   means for replacing each estimated value determined to be inaccurate.

10. The apparatus of claim 8, wherein, for a given estimated value, the means for assessing is further configured for:
   determining the infra-test value by subtracting a desired value from the estimated value; and
   determining the supra-test value by adding the desired value to the estimated value.

* * * * *